US010780437B2

(12) United States Patent
Zheng et al.

(10) Patent No.: US 10,780,437 B2
(45) Date of Patent: Sep. 22, 2020

(54) MICROFLUIDIC SYSTEM AND METHOD OF CONTROLLING PARTICLES BASED ON ARTIFICIALLY STRUCTURED ACOUSTIC FIELD

(71) Applicant: SHENZHEN INSTITUTES OF ADVANCED TECHNOLOGY, CHINESE ACADEMY OF SCIENCES, Shenzhen (CN)

(72) Inventors: Hairong Zheng, Shenzhen (CN); Fei Li, Shenzhen (CN); Feiyan Cai, Shenzhen (CN); Long Meng, Shenzhen (CN); Chen Wang, Shenzhen (CN); Chengxiang Zhang, Shenzhen (CN); Weibao Qiu, Shenzhen (CN); Yongchuan Li, Shenzhen (CN); Fei Yan, Shenzhen (CN); Lili Niu, Shenzhen (CN); Liufeng Geng, Shenzhen (CN); Chaowei Xu, Shenzhen (CN)

(73) Assignee: SHENZHEN INSTITUTES OF ADVANCED TECHNOLOGY, CHINESE ACADEMY OF SCIENCES, Shenzhen (CN)

(*) Notice: Subject to any disclaimer, the term of this patent is extended or adjusted under 35 U.S.C. 154(b) by 218 days.

(21) Appl. No.: 15/742,491

(22) PCT Filed: Oct. 10, 2015

(86) PCT No.: PCT/CN2015/091686
§ 371 (c)(1),
(2) Date: Jan. 5, 2018

(87) PCT Pub. No.: WO2017/059604
PCT Pub. Date: Apr. 13, 2017

(65) Prior Publication Data
US 2018/0369815 A1 Dec. 27, 2018

(51) Int. Cl.
B01L 3/00 (2006.01)
C12N 13/00 (2006.01)
(Continued)

(52) U.S. Cl.
CPC ... B01L 3/502761 (2013.01); B01L 3/502715 (2013.01); B01L 3/502792 (2013.01);
(Continued)

(58) Field of Classification Search
CPC ........ B01L 3/502761; B01L 3/502792; B01L 3/502715; B01L 2400/0439;
(Continued)

(56) References Cited

U.S. PATENT DOCUMENTS 8,679,338 B2 * 3/2014 Rietman ............... B01D 65/00
210/321.87
9,695,063 B2 * 7/2017 Rietman ............... B01D 61/00
(Continued)

FOREIGN PATENT DOCUMENTS

WO WO2014139260 * 9/2014 ............... B07C 5/34

OTHER PUBLICATIONS

Wilson et al. "Phononic crystal structures for acoustically driven microfluidic manipulations" Lab Chip, 2011, 11, 323-328 (Year: 2011).*
(Continued)

Primary Examiner — Benjamin R Whatley
Assistant Examiner — Quocan B Vo

(57) ABSTRACT

Disclosed is a microfluidic system based on an artificially structured acoustic field, comprising a microcavity used to accommodate a solution containing particles and a ultrasonic emission device used to emit ultrasound, and further comprising a phononic crystal plate placed in the microcavity. The phononic crystal plate has an artificial cycle structure, and is used to modulate the acoustic field so as to
(Continued)

control the particles. Also disclosed is a method of controlling microfluid particles based on an artificially structured acoustic field. In the particular embodiments, since a microcavity, an ultrasonic emission device and a phononic crystal plate are comprised, the ultrasonic emission device is used to emit ultrasound, and the phononic crystal plate has an artificial cycle structure, and is used to modulate the acoustic field so as to control the particles.

13 Claims, 8 Drawing Sheets

(51) Int. Cl.
  *G01N 15/10* (2006.01)
  *G01N 15/00* (2006.01)
(52) U.S. Cl.
  CPC .......... *C12N 13/00* (2013.01); *B01L 3/50273* (2013.01); *B01L 2200/0647* (2013.01); *B01L 2200/0652* (2013.01); *B01L 2300/06* (2013.01); *B01L 2300/08* (2013.01); *B01L 2300/0809* (2013.01); *B01L 2400/0436* (2013.01); *B01L 2400/0439* (2013.01); *B01L 2400/0496* (2013.01); *G01N 2015/0038* (2013.01); *G01N 2015/1006* (2013.01)
(58) Field of Classification Search
  CPC ..... B01L 2400/0436; B01L 2200/0647; B01L 3/50273; B01L 2200/0652; B01L 2300/06; B01L 2300/08; B01L 2300/0809; B01L 2400/0496; C12N 13/00; G01N 2015/1006; G01N 2015/0038
  See application file for complete search history.

(56) References Cited

U.S. PATENT DOCUMENTS

| | | | | |
|---|---|---|---|---|
| 2006/0286488 | A1* | 12/2006 | Rogers | B82B 3/00 430/325 |
| 2009/0098027 | A1* | 4/2009 | Tabata | B01F 11/0266 422/128 |
| 2012/0149126 | A1* | 6/2012 | Wilson | B01F 11/0266 436/175 |
| 2013/0330247 | A1* | 12/2013 | Wilson | G01N 29/222 422/504 |
| 2014/0305510 | A1* | 10/2014 | Piazza | B01L 3/50273 137/13 |

OTHER PUBLICATIONS

Li et al. "Phononic-Crystal-Based Acoustic Sieve for Tunable Manipulations of Particles by a Highly Localized Radiation Force", Physical Review Applied 1, 051001 (2014) (Year: 2014).*
Jimenez et al. "High-order acoustic Bessel beam generation by spiral gratings" Physics Procedia 70 Sep. 19, 2015 245-248 (Year: 2015).*
Nava et al. "All-silica microfluidic optical stretcher with coustophoretic prefocusing" Microfluid Nanofluid Jun. 16, 2015, 19:837-844 (Year: 2015).*
Isben et al. "Fluorescent microscope system to monitor real-time interactions between focused ultrasound, echogenic drug delivery vehicles, and live cell membranes", Ultrasonics 53 (2013) 178-184 (Year: 2013).*
Wu et al. "Reparable sonoporation generated by microstreaming" The Journal of the Acoustical Society of America 111, 1460 (2002) (Year: 2002).*
Wang et al. "Dexterous acoustic trapping and patterning of particles assisted by phononic crystal plate" Appl. Phys. Lett. 106, 163504 Apr. 22, 2015 (Year: 2015).*

* cited by examiner

MICROFLUIDIC SYSTEM AND METHOD OF CONTROLLING PARTICLES BASED ON ARTIFICIALLY STRUCTURED ACOUSTIC FIELD

CROSS REFERENCE TO RELATED APPLICATION

The present application is the U.S. national phase of PCT Application PCT/CN2015/091686 filed on Oct. 10, 2015, the disclosure of which is incorporated herein by reference in its entirety.

TECHNICAL FIELD

The present disclosure relates to a microfluidic control technique, particularly to a microfluidic system and a method of manipulating particles based on an artificial structure tuned acoustic field.

BACKGROUND

The microfluidic chip is also called Lab on a chip, it has the advantage of miniaturization, integration, high-throughput, low energy consumption, rapid analysis, and now it is widely used in biology, chemistry, medicine, environment and other fields. During the microfluidic analysis and detection process, micro/nano-particles such as cells, DNA, proteins, polystyrene microspheres and micro/nano- gold need to be transported through the microfluidic to functional units such as sample preparation, reaction, separation and detection. Thus, precise and fast micro/nano-particle transport technology provides the necessary power and precise control of the flowing of microfluidic, which is the most important function module of a microfluidic device.

Current technology of micro/nano-particles transport is mainly achieved by means of the combined effects of a microfluidic pump, a microfluidic cavity, microfluidic valves and other microfluidic devices. According to the classification of the microfluidic pump, these micro/nano-particle transport technologies can be divided into the passive type and the active type. The passive type techniques using microfluidic's own characteristics, such as surface tension as a driving force, and therefore does not require complex and expensive peripheral equipment, thus is suited for various portable microfluidic devices. However, since the passive type technique cannot flexibly regulate in real time the flow direction and the flow rate as required, therefore, the passive type technique is not suitable for the field such as biochemical immunoassay which needs complicated multiple steps of operating the microfluidic. Compared with the passive type technique, the active type technique based on mechanism of photodynamic, electroosmotic, electrophoresis, magnetophoresis, dielectrophoresis or acoustofluidics is mainly using external physical fields such as electric fields, magnetic fields, optical fields and acoustic fields to drive the microfluidic flowing, thus can provide more flexible operation of the microfluidic. However, the active type technique may have drawbacks such as complex process, introduction of moving parts and the unstable performance. In additional, since the above microfluidic techniques need to be performed within the microchannel, so there is a problem that the microchannel may be plugged by suspended particles, which limits the throughput and the number of uses of the device.

Micro-cavity based microfluidic device without microfluidic channels not only has simpler processing, but also has the advantage of avoiding the clogging of the microchannel, and therefore become the new trend of research and development of the microfluidic device. By using the electric field, a micro-cavity based microfluidic device for liquid droplets has been developed, but the system is not suitable for continuous flow. Based on the MEMS process, $A_0$ mode Lamb waves produced by stimulating the ZnO films to vibrate by an interdigital transducer can induce the acoustic streaming effect to transport micro-nano particles, but the flow generated by this process is entire linear flow, it is difficult to change the direction of flow to form complex path as required. In recent years, the acoustic microstreaming generated by using the oscillating bubbles achieve the transportation of the micro/nano-particles, but because of the non-uniform, unstable, difficulty in trappingbubbles, it is difficult to form a complicated transport path by constructing a bubble array as needed. Thus, under the condition of continuous flow, transporting the micro/nano-particles along an arbitrary path in the micro-cavity becomes a challenge, which restricts the development of micro-cavity based microfluidic devices.

In the field of drug delivery technology, safe and efficient drug delivery technology is the key technology in field of drug development, cancer research, pluripotent stem cell induction and tissue engineering. Therefore, the study and develop of safe and reliable, efficient and accurate, easy to operate drug delivery technology has become one of the frontiers of high-profile.

The current drug delivery technologies are mainly divided into three types: the biology method, the chemistry method and the physical method. The biological methods i.e., the viral-mediated delivery technique, has advantages of high efficiency and easy to operate. However, there are problems of immunogenicity, cytotoxicity and carcinogenicity. Therefore it is difficult to guarantee the safety. The chemical method is a method widely used in the current study, including cationic liposome method, cationic polymer method, cationic amino acids method, etc. This method has low efficiency, and depends on the cell type, and may have the problem of drug leakage and low stability.

Compared with the aforementioned two methods, the physical delivery method has the advantages of simple and safety. It mainly includes microinjection method, electroporation method, laser method and ultrasound method (sonoporation), etc. For the microinjection method, nucleic acid is injected directly into the cytoplasm or nucleus through microtubules, thus this method is not suitable for systemic delivery, requires higher operation skill, and usually causes cell death. The electroporation method is a simple, fast, high throughput, and most widely used method for physical delivery. The method utilizes high intensity electric pulses to cause perforation of the cell membrane, enhance the permeability of the cell membranes, thus the drug may pass through the hole into the cytoplasm. However, the electroporation method has higher rate of cell death. The laser method uses laser pulses to radiate the cell membrane to generate instantaneous holes, and then the exogenous nucleic acid is delivered to the cells. By using this method, appointed holes can be precisely implemented on a cell membrane, but the laser system is expensive.

Ultrasound induced drug delivery technology has received widespread attention due to its advantage of non-contact, non-invasive, inexpensive and universal applicability. Similar to the electroporation method, current ultrasound induced drug delivery technology is achieved by the biophysical process of cell perforation based on ultrasound combined with ultrasound contrast agent micro-bubbles.

This process is also known as sonoporation: inertial cavitation or steady state cavitation of micro-bubbles in acoustic field, and subsequent acoustic radiation force, microjet, micro-streaming or shear force can generate repairable holes with size of dozens of nanometers to several hundred nanometers on the cell surface, thus increasing the permeability of the cell membrane, so that the extracellular DNA, protein and other biological macromolecules can pass through the holes into the cells. However, micro-bubbles are unstable, have non-uniform sizes, thus it is difficult to perform precise control of the cavitation of the micro-bubble population.

SUMMARY

The present application provides a microfluidic system based on artificial structure tuned acoustic field and a method of manipulation of particles.

According to a first aspect of the present disclosure, the present application provides a microfluidic system based on artificial structure tuned acoustic field, including a micro-cavity and an ultrasonic wave transmitting device, the micro-cavity is used to contain a solution containing particles, the ultrasonic wave transmitting device is used for transmitting ultrasonic waves, further including a phononic crystal plate disposed in the micro-cavity, the phononic crystal plate is an periodically artificial structure, and is used to modulate the acoustic field to manipulate the particles.

According to a second aspect of the present disclosure, the present application provides a method of manipulating particles by microfluidic based on periodically artificial structure tuned acoustic field, including:

placing a phononic crystal plate in a micro-cavity, the phononic crystal plate is an periodically artificial structure;

adding a solution containing particles;

transmitting ultrasonic waves by an ultrasonic wave transmitting device, and modulating the acoustic field by the phononic crystal plate;

manipulating the particles by the phononic crystal plate based on the modulation.

With the above technical solutions, the present application may have beneficial effects in that:

In an embodiment of the present disclosure, since it includes the micro-cavity the ultrasonic wave transmitting device and the phononic crystal plate, the ultrasonic wave transmitting device can be used for transmitting ultrasonic waves, the phononic crystal plate is a periodicallyartificial structure used for modulating the acoustic field to manipulate particles, thus provides a novel approach for drug delivery, and provides technical support for drug development.

DETAILED DESCRIPTION

The present application will be further described in detail by specific embodiments with accompanying drawings.

The microfluidic system based on periodically artificial structure tuned acoustic field of the present disclosure has a smaller size, for example, in one embodiment, the size of the piezoelectric ceramic sheet is less than 2 cm, the width and length of the phononic crystal plate is 15 mm*20 mm, the height of the PDMS water tank is only 4 mm, the entire system is fabricated and integrated on a 50 mm*50 mm*1 mm Quartz glass plate, and the phononic crystal plate is positioned above the piezoelectric ceramic sheet. Therefore it is possible to manipulate and study particles such as cells less than 30 microns under a microscope. Accordingly, the present chip system may be combined with the microfluidics technology to manipulate and study particles such as cells less than 30 microns under a microscope.

Embodiment I

Figure 1:
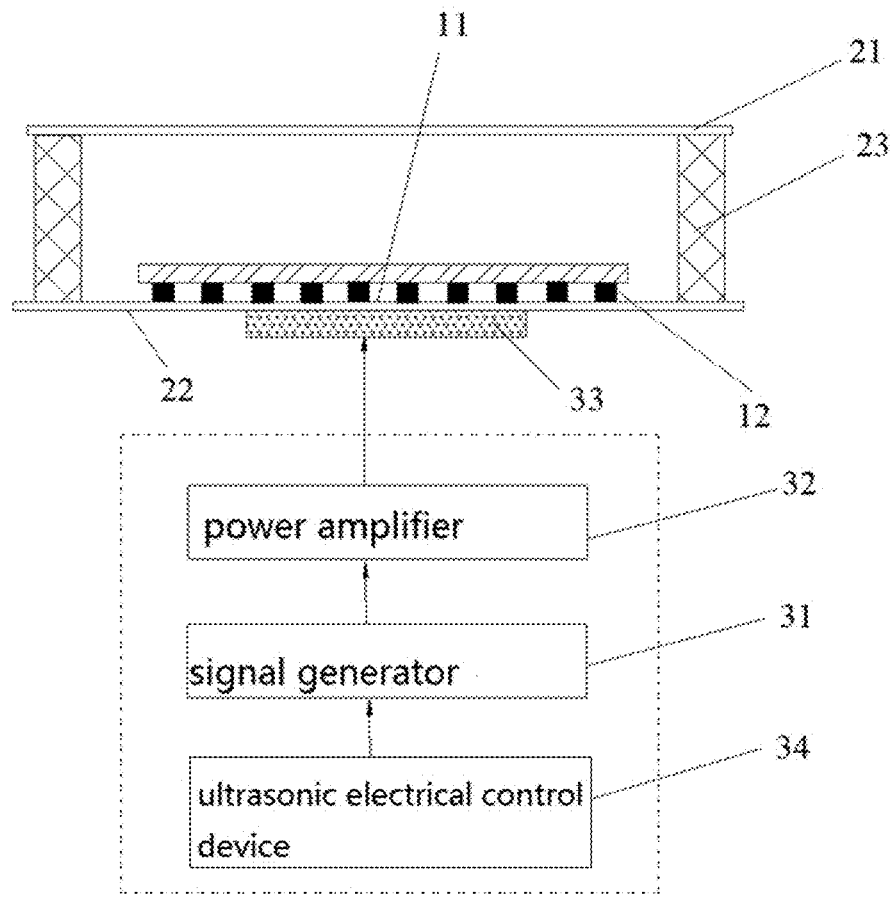
FIG. 1 is a structural schematic diagram of the system of the present application according to one embodiment.

Please refer to FIG. 1, it is a schematic diagram of the microfluidic system based on periodically artificial structure tuned acoustic field of the present application, according to one of the embodiments, it may include a micro-cavity, and ultrasonic wave transmitting device and a phononic crystal plate, the ultrasonic wave transmitting device is used for transmitting ultrasonic waves, the micro-cavity is used to contain a solution containing particles, the phononic crystal plate is positioned in the micro-cavity, and the phononic crystal plate is an periodically artificial structure for modulating the acoustic field to manipulate the particles. In the present application, the particle include micro/nano-particle and/or cells, the phononic crystal plate is used for modulating the acoustic field to drive the micro/nano-particles transporting along a designed path. The phononic crystal plate is configured to modulate the acoustic field to trap and align the cells to form a cell array. The phononic crystal plate may also be used to generate an array of micro-vortex to produce shear force to the cell array, thus to induce the cell schizolysis or the regulatable sonoporation. Since the phononic crystal plates are configured to generate acoustic radiation force to capture and arrange the cells to form a cell array, and generate an array of micro-vortex to produce quantitative regulatable shear force to the cell array, thereby provides repeatable, statistically significant and accurately quantitative regulatable sonoporation to multiple types of and large-scale cells.

Figure 2:
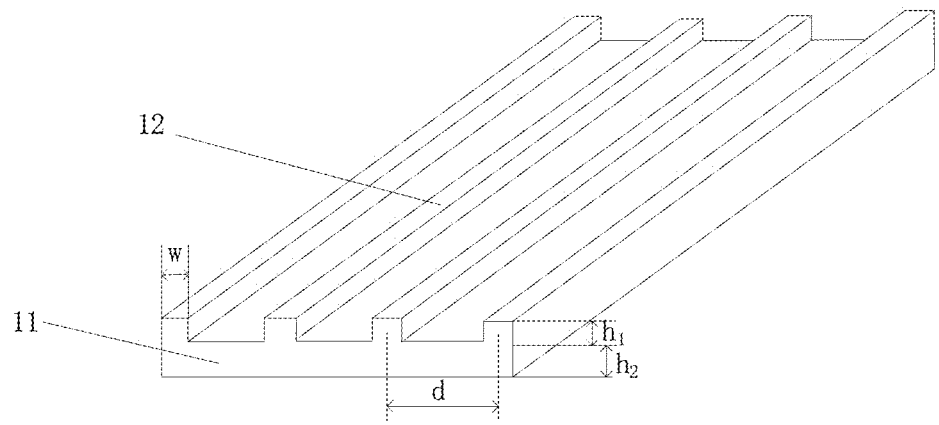
FIG. 2 is a structural diagram of the phononic crystal plate according to an embodiment of the present disclosure.
Figure 13:
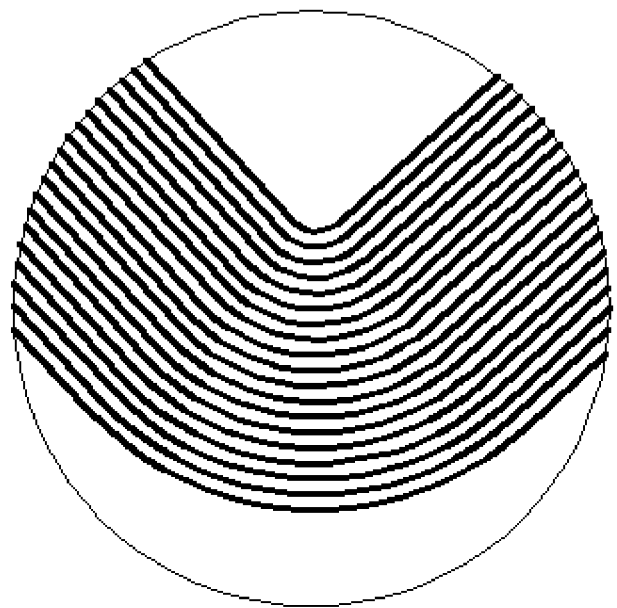
FIG. 13 is a structural diagram of the phononic crystal plate according to another embodiment of the present disclosure.
Figure 13:
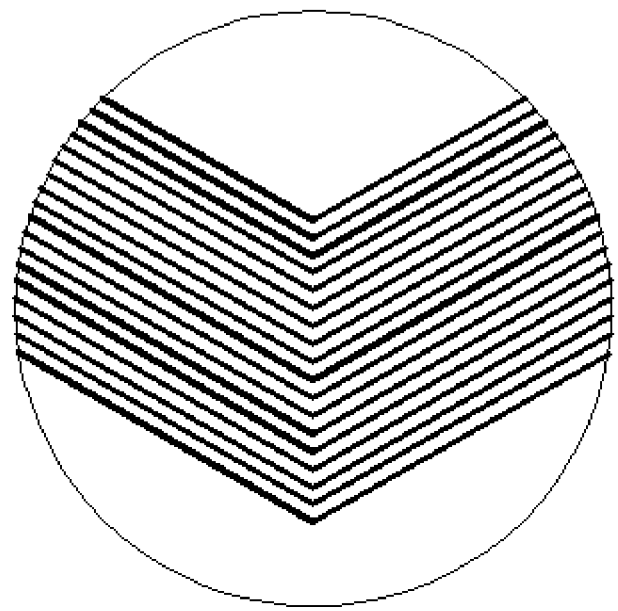
Figure 13:
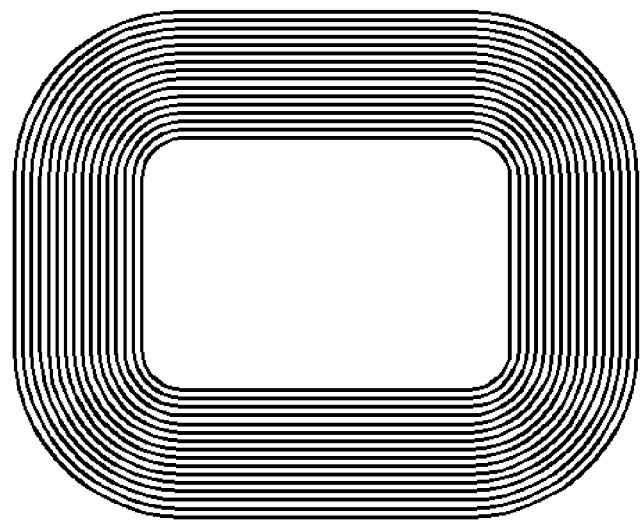

Please refer to FIG. 2, the phononic crystal plate may include a substrate 11 and ridges 12, the ridges 12 are disposed on the lower surface of the substrate 11, a plurality of ridges 12 are arranged in parallel with identical intervals. In one embodiment, the ridge 12 is curved or has a shape of closed loop. Patterns of the periodically artificial structure may be configured as required, for example, the shape of the ridges may appear as a line segment, or line segments connected with a 90 degree corner, line segments connected with a 120 degree corner, or line segments connected with a plurality of 90 degree corners or a loop composed of a plurality of line segments, thus to form a linear phononic crystal plate, a 90 degree corner phononic crystal plate, a 120 degree corner phononic crystal plate or a loop phononic crystal plate, respectively. The 90 degree corner phononic crystal plate is shown as in FIG. 13(a), the 120 degree corner phononic crystal plate is shown in FIG. 13(b), and the loop phononic crystal plate is shown in FIG. 13(c).

The cross section of the ridge may be rectangular, triangular, polygonal or semicircular. In the present embodiment, cross sections of the ridges are rectangular, the distance between the central lines of the rectangles is d, the thickness of the substrate is h2, and $0.15 \leq h2/d \leq 0.25$. The distance d between the central lines of the rectangular is the period of the periodically artificial structure. The periodically artificial structure may be made of rigid materials, particularly rigid materials with transverse wave speed greater than longitudinal wave speed of medium, namely water. The rigid material may be a metallic material, such as copper, aluminum, steel or other metallic materials. The rigid material may also be non-metallic material, such as glass. In one embodiment, the periodically artificial structure is a fence structure with a period of 0.35 mm, a height of 0.05 mm and a width of 0.05 mm which is made on a stainless steel plate with a thickness of 0.1 mm. The dimensions of the periodically artificial structure may be configured according to needs.

In one embodiment, when the cross section of the ridge is rectangular, the width and height of the rectangle is equal to the thickness of the substrate. That is, if the width of the rectangle is w, the height of the rectangle is h1, then $w=h1=h2$. In the present embodiment, the periodically artificial structure is a fence structure with a period $d=0.35$ mm, a height $h1=0.05$ mm and a width $w=0.05$ mm which is made on a stainless steel with a thickness $h1+h2=0.1$ mm by chemical etching.

The ultrasonic wave transmitting device includes a signal generator, a power amplifier, and an ultrasonic transducer. The signal generator is configured for generating a electric signal. The power amplifier is configured for amplifying the electric signal, and the ultrasonic transducer is configured for converting the amplified electric signal into ultrasound wave.

In one embodiment, the ultrasonic wave transmitting device includes a signal generator 31, a power amplifier 32 and an ultrasonic transducer 33. The signal generator 31 is configured for generating electric signals. The power amplifier 32 is configured for amplifying the electric signal, and the ultrasonic transducer is configured for converting the amplified electric signal to ultrasonic waves. The ultrasonic wave transmitting device may further include an ultrasonic electrical control device; the electronic control device may be used for setting parameters of the signal generator and the power amplifier, and controlling on or off of the ultrasonic transducer. The ultrasonic transducer may be one of the single element ultrasonic transducer, linear array ultrasonic transducer, two dimensional array ultrasonic transducer, phase array ultrasonic transducer and interdigital ultrasonic transducer. The resonance frequency of the artificial structure determines the driving frequency of the transmitted ultrasound wave, thus to determine the center frequency of the ultrasonic transducer. In the present embodiment, the ultrasonic transducer adopt a single array element ultrasonic transducer PZT4 or a 2×2 two dimensional array ultrasonic transducer composed of 4 single element ultrasonic transducers PZT4, or an 8×8 two dimensional array ultrasonic transducer composed of 64 single element ultrasonic transducers PZT4, and the center frequency thereof is 3.8 MHz. When capturing the micro/nano-particles and inducing the cell schizolysis or the regulatable sonoporation, the signal generator transmitting continuous sinusoidal signals having a frequency of 3.774 MHz. When transporting the micro/nano-particles, the signal generator Chrip pulse signals having a bandwidth of 3.774 MHz-3.979 MHz. In one embodiment, the signal generator may be a programmable signal generator (AFG3021, Tectronix), the power amplifier may be a 52 dB linear power amplifier (A300, E&I). Signals generated by the signal generator are amplified by the power amplifier to excite the ultrasonic transducer to generate ultrasonic waves, then to activate the phononic crystal plate.

The micro-cavity of the present application includes an upper base 21, a lower base 22 and side walls 23. The side walls enclose an interior cavity with openings at two ends, the openings go through with the interior cavity, and the upper base and the lower base are disposed at the openings respectively, i.e. the upper base is disposed at an upper opening and the lower base is disposed at a lower opening. The upper base and the lower base may be made of quartz glass, the side walls may be made of PDMS (polydimethylsiloxane) or glass. In one embodiment, the micro-cavity is rectangular and includes an upper base made of quartz glass, a lower base made of quartz glass and four side walls made of PDMS, the height thereof can be configured as desired. In the present embodiment, the height of the micro-cavity is 4 mm.

In particular embodiments of the present disclosure, the phononic crystal plate is a periodically artificial structure by etching a thin metal or non-metal plate, pattern of the structure determines the transport path of the micro/nano-particles. By using phononic crystals plates with different patterns, a large number of micro/nano-particles transporting along arbitrary designed paths can be achieved. By configuring different excitation parameters, a large number of micro/nano-particles can be flexibly switched between a trapping mode and a transport mode. By setting different excitation voltages, quantitative regulation of micro vortex streaming field can be achieved; thereby shear forces applied to the cell can be quantitatively regulated to control the degree of perforation. Accordingly, the present application realizes a simple, reliable, disposable, templated, programmable, parallel processed, high-throughput, multi-functional new microfluidic device.

Embodiment II

Figure 3:
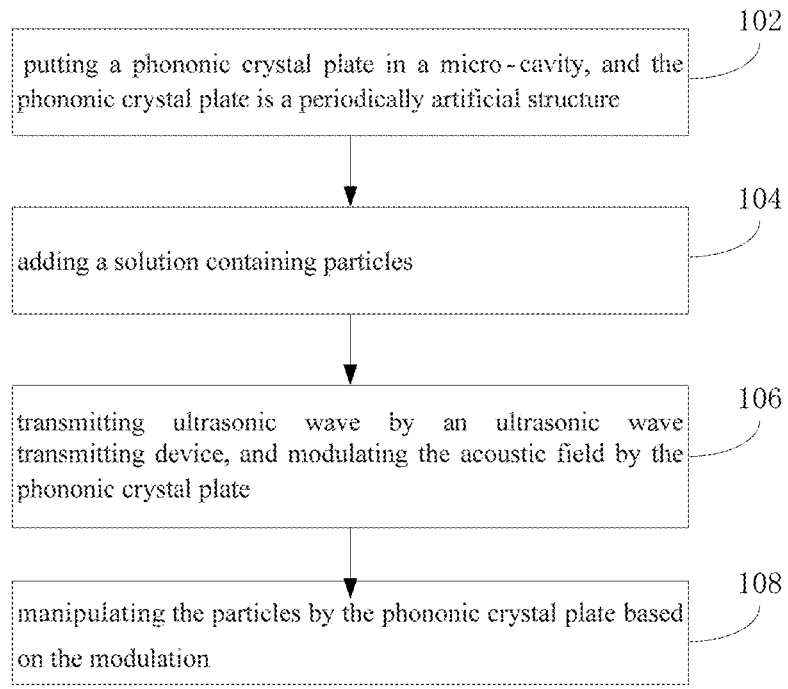
FIG. 3 is a flowchart of a method according to an embodiment of the present disclosure.

As shown in FIG. 3, an embodiment of the method of manipulating particles by microfluidic based on artificially structured acoustic field according to the present disclosure includes the steps of:

Step 102: putting a phononic crystal plate in a microcavity and the phononic crystal plate is a periodically artificial structure.

Step 104: adding a solution containing particles.

Step 106: transmitting ultrasonic wave by an ultrasonic wave transmitting device, and modulating the acoustic field by the phononic crystal plate.

Step 108: manipulating the particles by the phononic crystal plate based on the modulation.

Where the step 108 specifically includes:

Step 1082: the phononic crystal plate transporting the micro/nano-particles based on the modulated acoustic field;

The acoustic radiation force generated by the phononic crystal plate modulated acoustic field arranging and capturing cells to form a cell array, and generating micro vortex array to generate shear force to the cell array, or inducing cell schizolysis or regulatable sonoporation.

In one embodiment, step 108 may further include:

Step 1084: adjusting the transporting path of the micro/nano-particles by setting pattern of the ridge arrangement on the phononic crystal plate;

It can adjust the dimension of the micro-vortex array by setting the thickness of the substrate of the phononic crystal plate and the spacing between the ridges.

Where the step 106 may specifically include:

Step 1062: the center frequency of the signal is the resonance frequency of the phononic crystal plate when the ultrasonic wave transmitting device is used to transmit pulse waves, and the bandwidth is 15%~100%. The regulation of the transport velocity can be achieved by way of changing the voltage.

When the ultrasonic transmitting device is used to transmit continuous wave, the trapping of micro/nano-particles can be achieved by way of setting a driving frequency as the resonance frequency of the phononic crystal plate.

In one embodiment, step 106 may further include:

Step 1064: the ultrasonic wave transmitting device quantitatively regulating the micro-vortex array by adjusting the parameters thereof, thereby quantitatively regulating the shear force applied to the cells to control the degree of perforation, to achieve the cell schizolysis or induce the sonoporation. The excitation parameter includes voltage, driving frequency, pulse repetition frequency and pulse duration time.

In another embodiment, step 106 may further include:

Step 1066: the center frequency of the signal is the resonance frequency of the phononic crystal plate when the ultrasonic wave transmitting device is used to transmit sinusoidal pulse signal; by adjusting the parameters, quantitatively regulating the micro-vortex induced by the phononic crystal plate, thus regulating the shear force applied to the cells to control the degree of perforation.

When the transmitting device is used to transmit ultrasonic continuous wave, the driving frequency is set as the resonance frequency of the phononic crystal plate. By way of adjusting the excitation voltage, quantitatively regulating the micro-vortex induced by the artificially structured acoustic field, thus regulating the shear force applied to the cells to control the perforation.

Figure 4:
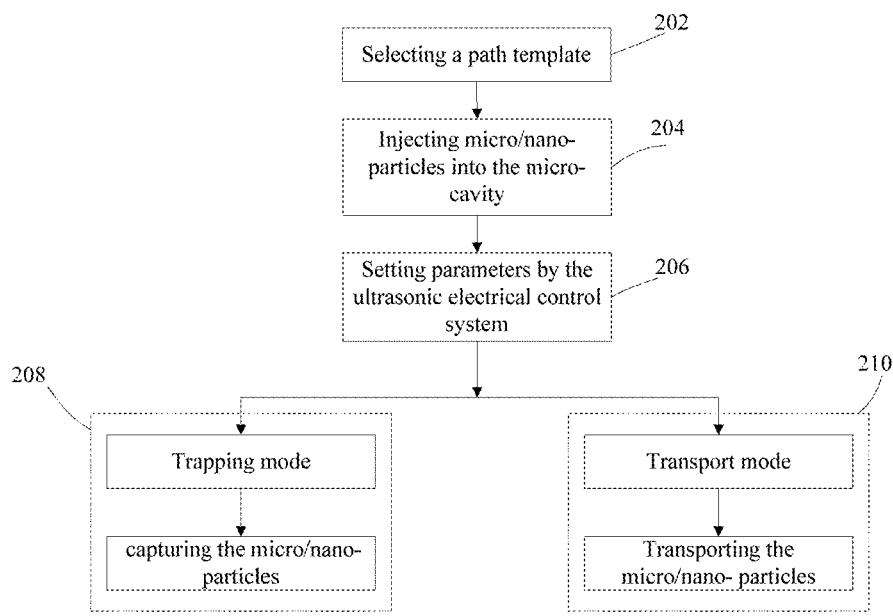
FIG. 4 is a flowchart of a method according to another embodiment of the present disclosure.

As shown in FIG. 4, it is a specific application example of the method of manipulating particles by microfluidic based on artificial structure tuned acoustic field according to the present application, i.e., an implementation method of transporting micro/nano-particles, including the steps of:

Step 202: selecting suitable phononic crystal plate according to requirement.

Step 204: injecting micro/nano-particles into the microcavity;

In the present embodiment, the micro/nano-particles can be polystyrene microspheres, in particular a diameter of the polystyrene microsphere is 15 μm 74964-10ML-F.

Step 206: set the parameters of a signal generator and a power amplifier by an ultrasonic electrical control system;

Step 208: capturing the micro/nano-particles in the trapping mode;

Step 210: transporting the micro/nano-particles in the transport mode. The transport velocity can be quantitatively regulated by adjusting the voltage.

In one embodiment, step 206 of the method of manipulating particles by microfluidic based on artificial structure tuned acoustic field of present disclosure may include:

When capturing the micro/nano-particles, the signal generator emits a continuous sinusoidal signal having a frequency of 3.774 MHz. When transporting the micro/nano-particles, the signal generator emits Chirp pulse signal with a bandwidth of 3.774 MHz-3.979 MHz. The transport speed can be quantitatively regulated by adjusting the voltage.

Figure 5:
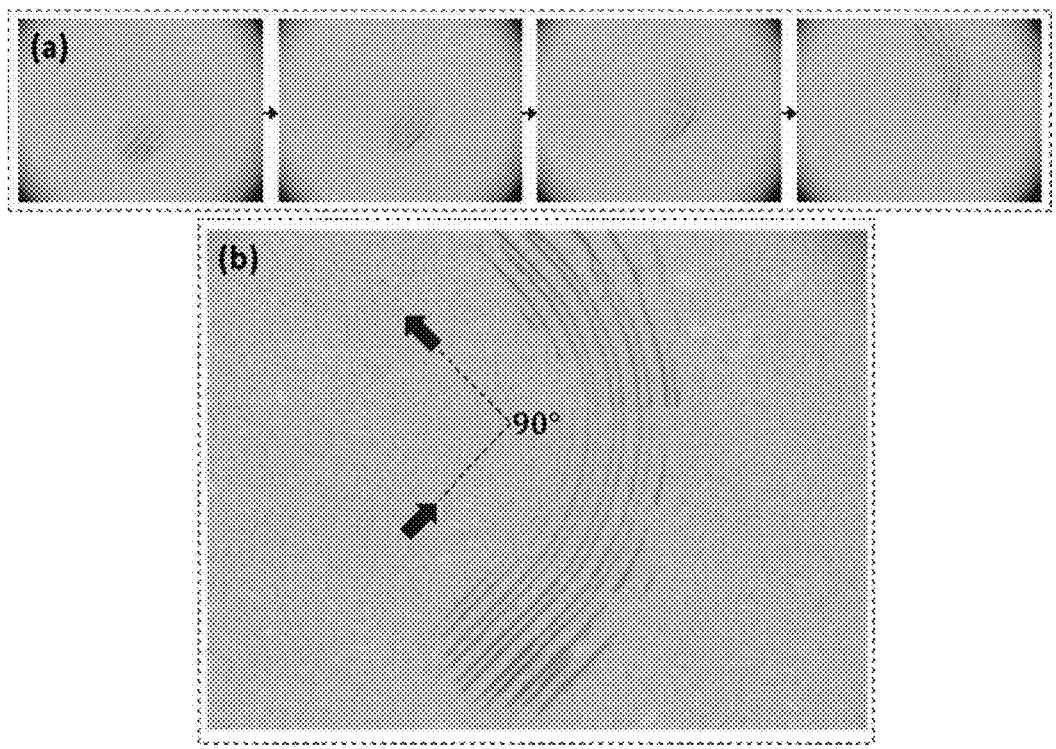
FIG. 5 is an effect diagram of transporting micro/nano-particles along a phononic crystal plate with a 90 degree corner according to the present disclosure.

FIG. 5 shows an effect diagram of 15 micron polystyrene microspheres transporting along a 90 degree corner path template. The signal generator emits Chirp pulse signal with a bandwidth of 3.774MHz-3.979MHz, the pulse signal is delivered to the power amplifier to excite the ultrasonic transducer to generate ultrasonic waves. The ultrasonic wave drives the periodically artificial structure to vibrate to generate acoustic streaming on the surface of the structure. FIG. 5(a) is an image of the transporting process at different time by using a CCD camera. FIG. 5(b) is a joint image of different moments, which showing the track of the micro/nano-particles. From the beginning to the end, the micro/nano-particles move along the path as designed, and the direction of movement changes 90 degree.

Figure 6:
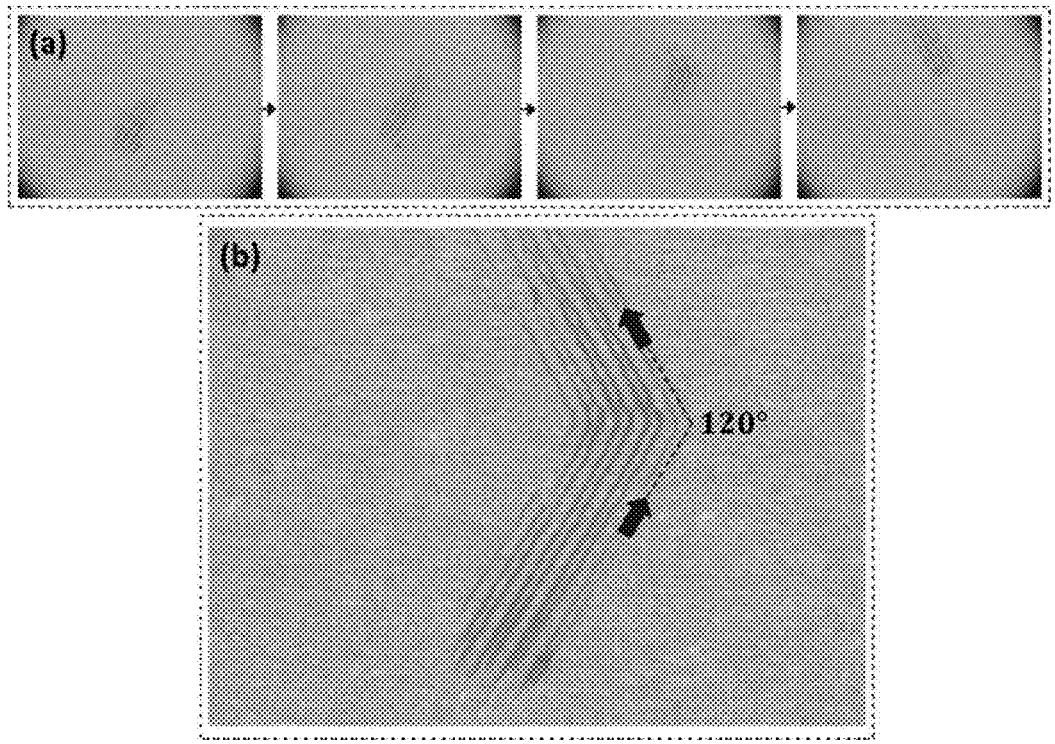
FIG. 6 is an effect diagram of transporting micro/nano-particles along a phononic crystal plate with a 120 degree corner according to the present disclosure.

FIG. 6 shows an effect diagram of 15 micron polystyrene microspheres transporting along a 120 degree corner path template. The signal generator emits Chirp pulse signal with a bandwidth of 3.774 MHz-3.979 MHz, the pulse signal is delivered to the power amplifier to excite the ultrasonic transducer to generate ultrasonic waves. The ultrasonic wave drives the periodically artificial structure to modulate the emitted acoustic field. FIG. 6(a) is an image of the transporting process at different time by using a CCD camera. FIG. 6(b) is a joint image of different moments, which showing the track of the micro/nano-particles. From the beginning to the end, the micro/nano-particles move along the path as designed, and the direction of movement changes 60 degree.

Figure 7:
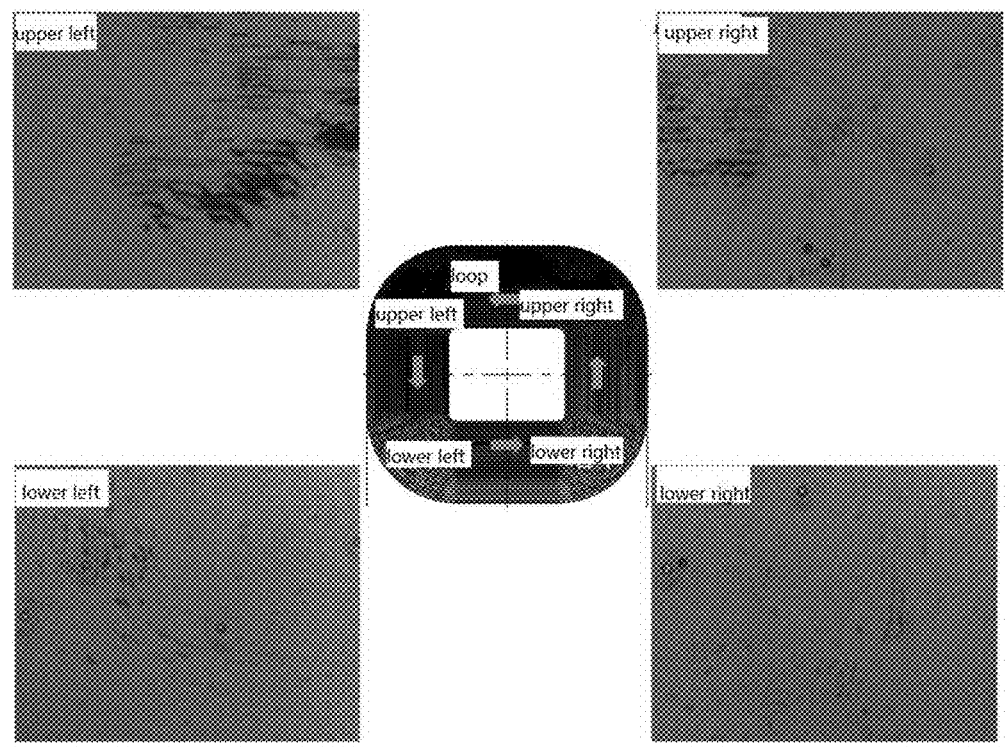
FIG. 7 is an effect diagram of transporting micro/nano-particles along a phononic crystal plate with a loop pattern according to the present disclosure.

FIG. 7 shows an effect diagram of 15 micron polystyrene microspheres transporting along a loop path template. The signal generator emits Chirp pulse signal with a bandwidth of 3.774 MHz-3.979 MHz, the pulse signal is delivered to the power amplifier to excite the ultrasonic transducer to generate ultrasonic waves. The ultrasonic wave drives the periodically artificial structure to vibrate to modulate the emitted acoustic field. The middle image shows that the movement path of the micro/nano-particles is a circuit loop, and the direction of movement is counterclockwise. The images of the transporting process at different time and different positions are photographed by using a CCD camera. At the very beginning, the micro/nano-particles are located in the region between the upper left and the upper right. Driven by the ultrasound, the periodically artificial structure vibrates to modulate the emitted acoustic field, thus to drive the micro/nano-particles sequentially passing through the four positions of upper left, the lower left, the lower right and the upper right of the loop in the counter-clockwise direction, and eventually back to the initial position. From the beginning to the end, the micro/nano-particles move along the path as designed, and the direction of movement changes 360 degree.

Figure 8:
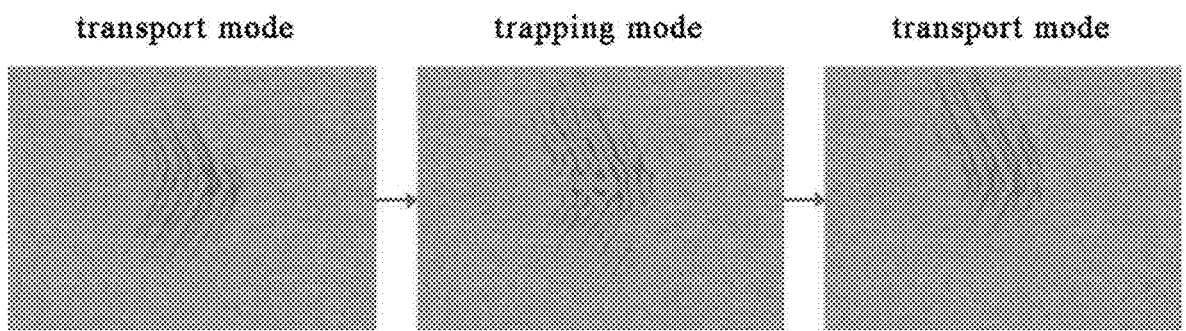
FIG. 8 is an effect diagram of switching between a transport mode and a trapping mode according to the present disclosure.

FIG. 8 is an effect diagram of switching between a trapping mode and a transport mode. When transporting the micro/nano-particles, the signal generator transmitting Chirp pulse signal with a bandwidth of 3.774 MHz-3.979 MHz. When capturing the micro/nano-particles, the signal generator transmitting a continuous sinusoidal signal of frequency 3.774 MHz. The images of the transporting process at different time are photographed by using a CCD camera. At the very beginning, under the excitation of the Chirp pulse, 15 micron particles transporting along the 120 degree corner path. When switched to excitation of a continuous sinusoidal signal, the 15 micron particles stops movement immediately and are trapped on the surface of the path template. When the excitation signal switches back to the Chirp signal, the captured 15 micron micro/nano-particles of continue to transport along the designed path.

Figure 9:
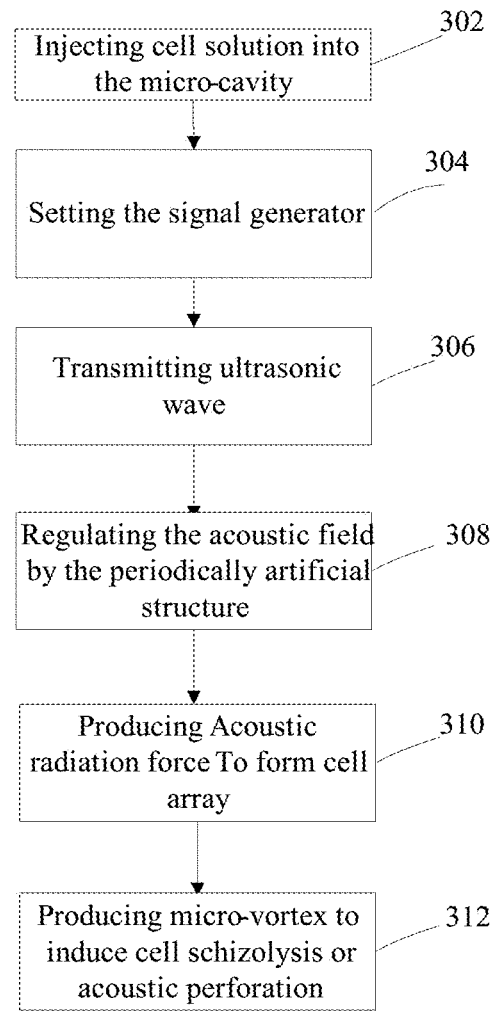
FIG. 9 is a flowchart of a new method of manipulating particles based on a periodically artificial structure tuned acoustic field of the present application when applied in an embodiment of large scale cell array schizolysis or perforation.

As shown in FIG. 9, it is another specific application example of the method of manipulating particles by microfluidic based on artificial structure tuned acoustic field according to the present application, that is, a method of large-scale cell array schizolysis or perforation, which includes the steps of:

Step 302: injecting cell solution into a micro-cavity. In the present embodiment, the cell can be selected from melanoma cells and breast tumor cells;

Step 302: setting a parameter of the signal generator;

Step 304: transmitting ultrasonic waves by the ultrasonic wave transmitting device;

Step 306: regulating the acoustic field by the periodically artificial structure;

Acoustic radiation force generated by the modulated acoustic field aligning and capturing cells to form a cell array, and generating micro-vortex array to generate shear force to the cell array, thus inducing cell schizolysis or regulatable sonoporation.

In one example of the method of manipulating particles by microfluidic based on artificial structure tuned acoustic field according to the present disclosure, the step 304 thereof specifically include:

The signal generator transmits a continuous sinusoidal signal or a pulse sinusoidal signal with a frequency of 3.774 MHz. By adjusting the voltage, driving frequency, pulse repetition frequency, pulse duration time and other parameters, the micro-vortex can be quantitatively regulated to quantitatively regulate shear forces applied to the cells, thus to control the perforation.

Figure 10:
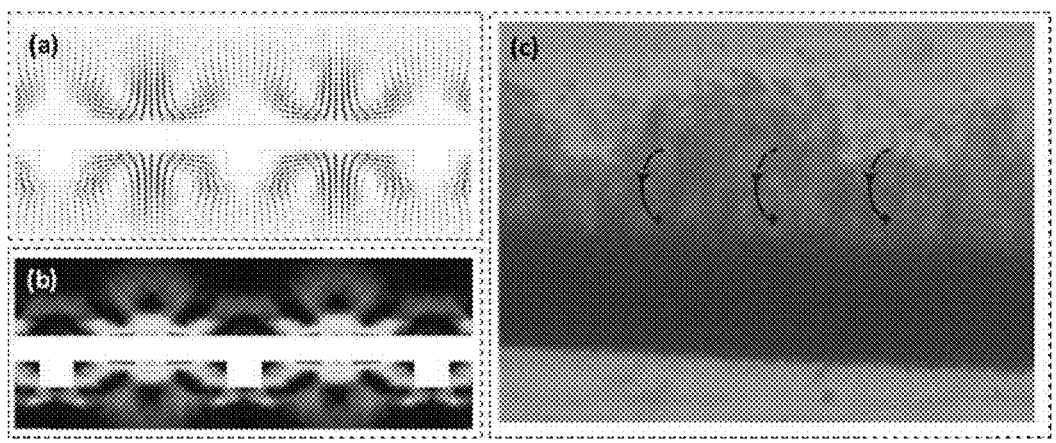
FIG. 10 is an effect diagram of micro-vortex and shear force generated by using the phononic crystal plate of the present disclosure to modulate the acoustic field.

FIG. 10 shows a micro-vortex and shear force generated by the phononic crystal plate modulated acoustic field. The signal generator generates a continuous sinusoidal signal with a frequency of 3.774 MHz, the signal is delivered to the power amplifier to excite the ultrasonic transducer to generate ultrasonic waves. The ultrasonic wave drives the periodically artificial structure to vibrate to generate micro-vortex on the surface of the structure. FIG. 10(a) is the calculated acoustic streaming field; FIG. 10(b) is a shear force distribution further calculated in accordance with the streaming field; FIG. 10(c) is the image of the micro-vortex recorded by the CCD camera.

Figure 11:
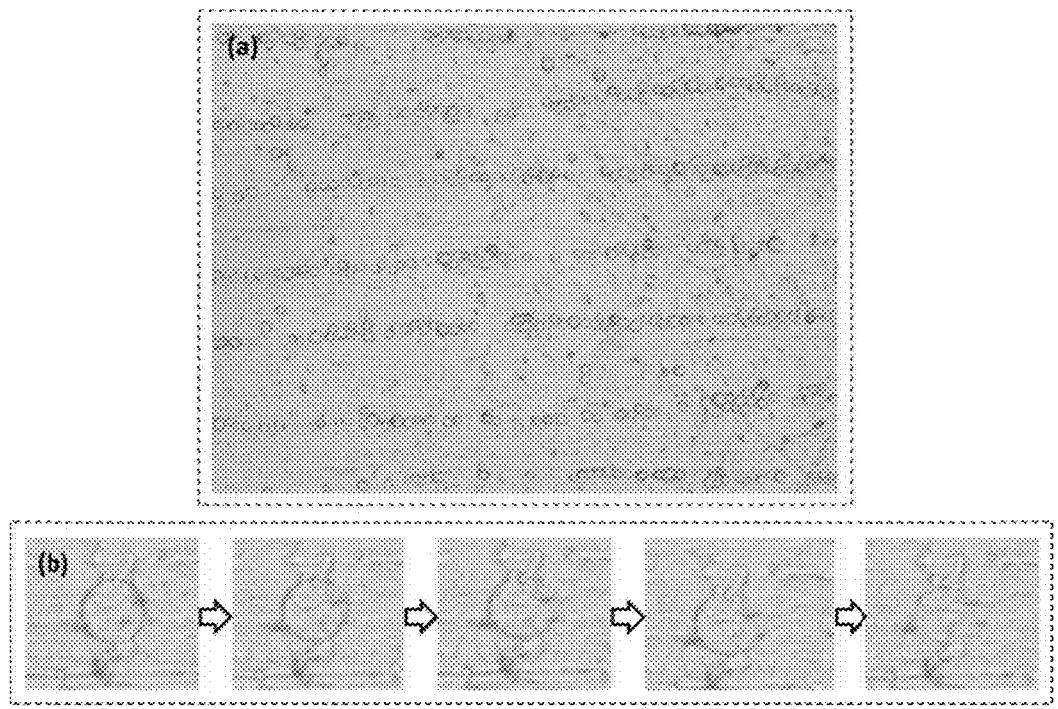
FIG. 11 is an effect diagram of a cell array formed by using the present disclosure and the cell schizolysis.

FIG. 11 shows a cell array formed of 15 micron melanoma cells and the process of schizolysis. The signal generator generates a continuous sinusoidal signal with a frequency of 3.774 MHz, the signal is delivered to the power amplifier to excite the ultrasonic transducer to generate ultrasonic waves. The ultrasonic wave activates the periodically artificial structure to vibrate to generate acoustic radiation force on the surface of the structure for aligning and capturing cells to form a cell array, shear forces generated by the micro-vortex applied to the cells produce the cell schizolysis. FIG. 11(a) is a cell array photographed by the CCD camera. FIG. 11(b) is the diagram showing the process of cell schizolysis in the cell array.

Figure 12:
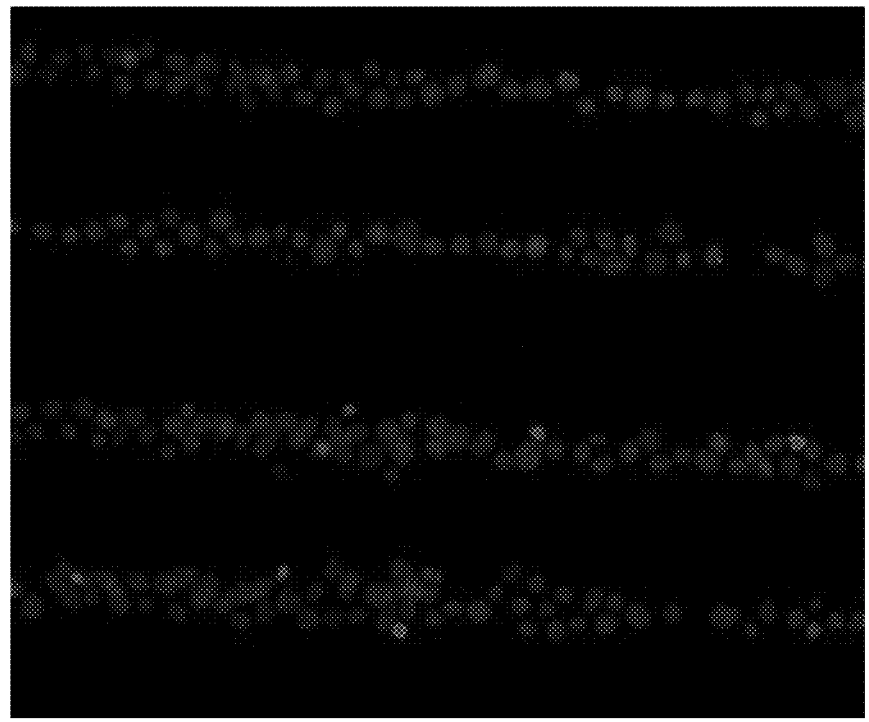
FIG. 12 is an effect diagram of a cell array formed by using the present disclosure and the cell perforation.

FIG. 12 shows an effect when drugs entered the cell when the 15 microns melanoma cell has been perforated. In the experiment, propidium iodide (PI) fluorescence dye is adopted. Before the perforation, no PI entered into the cell to dye it, therefore the cell cannot be observed under the fluorescence mode. After the perforation, PI entered into the cell from outside to dye it, therefore the cell can display red fluorescence.

In the embodiments of the application, since the phononic crystal plate includes a substrate and a plurality of ridges arranged in parallel with identical distance on a lower surface of the substrate, and the ridge is curved or has a shape of closed loop. By designing the pattern of the periodically artificial structure, the transporting path of the micro/nano-particle may be flexibly designed. By choosing phononic crystal plates with different patterns, transport paths of the micro/nano-particles can be changed. By utilizing the periodically artificial structure to modulate the acoustic field, the transport of a large number of micro/nano-particles along arbitrary designed paths in the micro-cavity simultaneously may be achieved. In the embodiments of the present application, by configuring different excitation parameters of the signal generator, the trapping and the transport of the micro-nano particles can be flexibly switched. In the process of microfluidic analysis, when the micro/nano-particles passing through the unit modules such as sample preparation, reaction and detection, the micro/nano-particles can be captured by the unit modules flowed through by altering the transmission parameters of the signal generator, thus to make analysis and testing of for the micro/nano-particles. When the analysis and test are completed, the parameters may be switched from the trapping mode parameters to the transport mode parameters, and the micro-nano particles are transported to the next analytical detection unit. In the specific embodiments of the present disclosure, a peridically artificial structure is used for modulating the acoustic field to generate acoustic radiation force for aligning and capturing cells to form a cell array, and generating an array of micro-vortex to produce quantifiable regulated shear force to the cell array. Compared with the conventional delivery technology of ultrasound combined with micro-bubbles, the present application do not need the intervention of micro-bubbles, thus the present application can provide repeatable, statistically significant and accurately quantitative regulatable sonoporation to massive cells.

The above content is described in further detail with reference to specific embodiments of the present invention, and should not be considered that the embodiments of the present invention are limited to these specific descriptions. To those ordinary skilled peoples in the art of the present invention, it can make various simple deductions or replacements without departing from the spirit of the present invention.

What is claimed is:

1. A microfluidic system based on artificial structure tuned acoustic field, comprising:

a micro-cavity and an ultrasonic wave transmitting device arranged outside the micro-cavity, wherein the microcavity is configured to contain a solution containing particles, the ultrasonic wave transmitting device is configured to transmit ultrasonic waves, wherein the system further comprises a phononic crystal plate disposed in the micro-cavity, the phononic crystal plate is a periodically artificial structure and configured to modulate an acoustic field to manipulate the particles, wherein such modulating comprising:

along a designed path on the phononic crystal plate, transporting the particles based on an acoustic radiation force induced by the acoustic field modulated by the phononic crystal plate; and capturing and aligning cells to form a cell array based on the acoustic radiation force generated by the acoustic field modulated by the phononic crystal plate, and generating a micro-vortex array to generate shear force to the cell array to induce a cell schizolysis or a regulatable sonoporation;

wherein the micro-cavity comprises an upper base, a lower base and side walls, wherein the side walls are configured to enclose an interior cavity with an opening at each end, and the upper base and the lower base are disposed at the openings respectively.

2. The system of claim 1, wherein the phononic crystal plate comprises a substrate and a plurality of ridges disposed at a lower surface of the substrate, the ridges disposed in parallel with identical intervals.

3. The system of claim 2, wherein the plurality of ridges comprise a fold line, a curved line or a closed loop.

4. The system of claim 3, wherein a cross section of each of the plurality of ridges is rectangular, triangular, polygonal or semicircular.

5. The system of claim 4, wherein the cross section of each of the plurality of ridges is a rectangle, and a distance between the central lines of the rectangle is d, a thickness of the substrate is h2, and $0.15 \leq h2/d \leq 0.25$.

6. The system of claim 5, wherein a width of the rectangle and a height of the rectangle are equal to the thickness of the substrate.

7. The system of claim 1, wherein the ultrasonic wave transmitting device comprises a signal generator, a power amplifier, an ultrasonic transducer and an ultrasonic electrical control device, the signal generator is configured to generate a transmission signal, the power amplifier is configured to amplify the transmitted signal, the ultrasonic transducer is configured to convert an amplified signal to the ultrasonic waves, the electronic control device is configured to set parameters of the signal generator and the power amplifier, and the electronic control device is configured to switch on or switch off the ultrasonic transducer.

8. The system of claim 1, wherein the upper base and the lower base are made of quartz glass, the side wall is made of PDMS or glass.

9. A method of manipulating particles by microfluidic based on artificial structure tuned acoustic field comprising:

placing a phononic crystal plate in a micro-cavity, wherein the phononic crystal plate is a periodically artificial structure, wherein the micro-cavity comprises an upper base, a lower base and side walls, wherein the side walls are configured to enclose an interior cavity with an opening at each end, and the upper base and the lower base are disposed at the openings respectively;

adding a solution containing particles;

transmitting ultrasonic waves by an ultrasonic wave transmitting device arranged outside the micro-cavity, and modulating an acoustic field by the phononic crystal plate; and manipulating the particles by the phononic crystal plate based on the modulation, which comprising:

along a designed path on the phononic crystal plate, transporting the particles based on an acoustic radiation force induced by the acoustic field modulated by the phononic crystal plate; and capturing and aligning cells to form a cell array based on the acoustic radiation force generated by the acoustic field modulated by the phononic crystal plate, and generating a micro-vortex array to generate shear force to the cell array to induce a cell schizolysis or a regulatable sonoporation.

10. The method of claim 9, wherein the manipulating the particles by the phononic crystal plate based on the modulation comprises:

adjusting a transport path of the particles by configuring a pattern of a ridge arrangement of the phononic crystal plate; and regulating a size of the micro-vortex array by configuring a thickness of the a substrate of the phononic crystal plate or a spacing of ridges.

11. The method of claim 9, wherein the transmitting ultrasonic waves by an ultrasonic wave transmitting device, and modulating an acoustic field by the phononic crystal plate comprises:

when the ultrasonic wave transmitting device is configured to transmit pulse waves, a center frequency of the signal is the resonance frequency of the phononic crystal plate, and the bandwidth is 15%~100%, and a regulation of a transport velocity is achieved by way of changing an voltage;

when the ultrasonic transmitting device is configured to transmit continuous wave, a driving frequency is configured as the resonance frequency of the phononic crystal plate to realized capturing of the particles.

12. The method of claim 9, wherein the transmitting ultrasonic waves by an ultrasonic wave transmitting device, and modulating an acoustic field by the phononic crystal plate further comprises:

regulating the micro-vortex array quantitatively by adjusting parameters of the ultrasonic wave transmitting device to quantitatively regulate the shear force applied to the cells to control the cell perforation, or achieve a cell schizolysis or a regulatable sonoporation, wherein the parameters comprise excitation voltage, driving frequency, pulse repetition frequency and pulse duration time.

13. The method of claim 12, wherein the transmitting ultrasonic waves by an ultrasonic wave transmitting device, and modulating an acoustic field by the phononic crystal plate further comprises:

when the ultrasonic wave transmitting device is configured for transmitting a sinusoidal pulse signal, a center frequency of the signal is the resonance frequency of the photonic crystal plate, quantitatively regulating the micro-vortex induced by the phononic crystal plate by adjusting the parameters to quantitatively regulate the shear force applied to the cells to control the cell perforation;

when the ultrasonic wave transmitting device is configured for transmitting a continuous wave, a driving frequency is configured as the resonance frequency of the phononic crystal plate, quantitatively regulating the micro-vortex induced by an artificial structure tuned acoustic field by adjusting an excitation voltage, thereby quantitatively regulate the shear force applied to the cells to control the cell perforation.

* * * * *